(12) United States Patent
Mori

(10) Patent No.: US 8,104,256 B2
(45) Date of Patent: Jan. 31, 2012

(54) IMAGING OPTICAL UNIT, INSPECTION METHOD FOR THE SAME, AND IMAGE READING APPARATUS

(75) Inventor: Seiichiro Mori, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 451 days.

(21) Appl. No.: 12/435,969

(22) Filed: May 5, 2009

(65) Prior Publication Data
US 2009/0279095 A1 Nov. 12, 2009

(30) Foreign Application Priority Data
May 8, 2008 (JP) .................................. 2008-122209

(51) Int. Cl.
*G01N 21/55* (2006.01)

(52) U.S. Cl. .......................................... 56/445; 356/448

(58) Field of Classification Search .......... 356/445–448, 356/450–458
See application file for complete search history.

(56) References Cited

U.S. PATENT DOCUMENTS

| 4,155,631 A | * | 5/1979 | Borsare et al. | ................. | 359/847 |
| 5,229,889 A | * | 7/1993 | Kittell | ............................ | 359/849 |
| 6,061,323 A | * | 5/2000 | Jerman et al. | ............... | 369/13.32 |
| 7,428,194 B2 | * | 9/2008 | Sohn et al. | ................. | 369/44.23 |

FOREIGN PATENT DOCUMENTS

| JP | H03-113961 A | 5/1991 |
| JP | H08-292371 A | 11/1996 |
| JP | 2004-133378 A | 4/2004 |

* cited by examiner

*Primary Examiner* — Gregory J Toatley
*Assistant Examiner* — Jarreas C Underwood
(74) *Attorney, Agent, or Firm* — Canon U.S.A., Inc. IP Divison

(57) ABSTRACT

Provided is an imaging optical unit used in an image reading apparatus for imaging image information on a photoelectric conversion element. The imaging optical unit includes a case and an imaging optical system having multiple reflecting members housed and disposed in the case. The reflecting member has a mirror surface for detecting assembly performance in the case on a side opposite to an optical surface for performing an imaging action. A light beam from a light source unit is projected to the mirror surface of the reflecting member and reflection light from the mirror surface is used for detecting one of a shift of posture and a distortion of the reflecting member.

12 Claims, 5 Drawing Sheets

IMAGING OPTICAL UNIT, INSPECTION METHOD FOR THE SAME, AND IMAGE READING APPARATUS

BACKGROUND OF THE INVENTION

1. Field of the Invention

The present invention relates to an imaging optical unit and an inspection method for the same. Particularly in an image scanner, a digital copying machine, a facsimile, or the like, the present invention can be used suitably for reading image information of a monochrome image or a color image using a signal from a line sensor (image pickup element or photoelectric conversion element).

2. Description of the Related Art

Conventionally, various flat bed type image scanners have been proposed as an image reading apparatus (image scanner) for reading image information on a surface of an original (see Japanese Patent Application Laid-Open No. H03-113961).

In the flat bed type image scanner, an imaging lens (imaging optical system) and a line sensor (CCD) are fixed while only a reflection mirror disposed in an optical path is moved so that the surface of the original is scanned by slit exposure for reading image information, which is called a 2:1 mirror scanning method.

In recent years, in order to simplify a structure of the apparatus, the reflection mirror, the imaging lens, the line sensor, and the like are incorporated as one unit to scan the surface of the original. This is called an integrated carriage type scanning method and has been adopted in many cases.

FIG. 9 is a schematic diagram of a main part of a conventional image reading apparatus adopting the integrated carriage type scanning method.

In FIG. 9, a light beam emitted from an illumination light source 81 illuminates an original 87 placed on an original table (original table glass) 82. Further, a reflection light beam from the illuminated original 87 bends its optical path inside a carriage 86 while being reflected by first, second and third reflection mirrors 83a, 83b and 83c in turn, and an imaging lens (imaging optical system) 84 condenses the light beam on a surface of a line sensor (image pickup element) 85 so as to form an image.

The line sensor 85 includes multiple light receiving elements aligned in a one-dimensional direction. In a case of FIG. 9, the light receiving elements are aligned in a direction perpendicular to a paper surface (corresponding to a main scanning direction).

Further, the carriage 86 is moved by a driving motor 88 in a direction of an arrow A illustrated in FIG. 9 (corresponding to a sub scanning direction) so that image information of the original 87 can be read in a two-dimensional manner.

FIG. 10 is an explanatory diagram of a fundamental structure of an imaging optical system of the image reading apparatus illustrated in FIG. 9.

In FIG. 10, numeral 84 denotes an imaging lens. A group of line sensors 85 includes line sensors 85R, 85G and 85B for reading red (R) color, green (G) color and blue (B) color. Read areas 87R, 87G and 87B on the surface of the original 87 correspond to the line sensors 85R, 85G and 85B, respectively. The surface of the original 87 is scanned in the sub scanning direction indicated by the arrow, whereby the same area is read by the line sensors 85R, 85G and 85B of different colors with a certain time interval.

Conventionally, it has been proposed variously that a non-coaxial optical system with aberration being corrected can be constructed by introducing a concept of a reference axis instead of an optical axis as the imaging optical system that is used for an image formation apparatus, in which a constitution surface becomes an asymmetric aspherical surface (see Japanese Patent Application Laid-Open No. H08-292371).

Japanese Patent Application Laid-Open No. H08-292371 discloses its designing method.

In addition, as an imaging optical system having a simpler structure, an imaging optical system having a small number of free-form curved surface mirrors (non-coaxial optical system) has been variously proposed (see Japanese Patent Application Laid-Open No. 2004-133378).

An off-axial optical system using optical elements having a free-form curved surface mirror has a non-coaxial constitution surface. With no vignetting occurring on a reflection surface, there is a merit that an optical system using the reflection surface can be constructed easily.

In addition, the off-axial optical system having only the reflection surface has a merit that no chromatic aberration occurs. Therefore, it is possible to meet a high demand about a numeric aperture or resolution because there is no color blur or shift unlike a conventional refraction optical system.

However, the off-axial optical system including the optical element having the reflection surface has a tendency to decrease its optical performance largely if a shape of the optical element changes or an off-center error occurs in the manufacturing process of the optical element.

Therefore, a reflection type optical element is required to have higher accuracy of a surface shape of each optical element and assembly thereof when assembled in a case compared with the case of using an optical element of a refraction system.

When the optical elements are housed and held in the case, it is very difficult to measure changes of shapes of the optical elements and an assembly error in the state where the optical elements are held, because the optical path is bent by the reflection and the reflection surfaces face each other inward in the entire system.

In particular, if design optical performance cannot be obtained as a whole, it is very difficult to specify which optical element is the cause.

Conventionally, all the optical elements should be removed from the case for measuring the change in shape (surface shape) of each optical element, and then each optical element is reassembled in the case if it has no problem.

Therefore, as to the imaging optical unit including the reflection type optical elements having the free-form curved surface, it is very difficult to inspect the change in shape of each optical element and to measure the assembly error or the like after the optical elements are once housed and held in the case.

In order to reduce a relative positional error of the optical elements and to increase the assembly accuracy, it is necessary to manufacture a holder member for holding the optical element with high accuracy. However, it is very difficult to manufacture the holder member with high accuracy.

SUMMARY OF THE INVENTION

It is an object of the present invention to provide an inspection method for an imaging optical unit that facilitates measuring a change in shape of each optical element and an assembly error and to inspect the same even if the imaging optical element including multiple reflection type optical elements is housed and held in the case.

According to the present invention, there is provided an inspection method for an imaging optical unit used in an image reading apparatus for obtaining image information by imaging the image information on a photoelectric conversion element, the imaging optical unit including a case and an imaging optical system disposed in the case, the imaging optical system including a reflecting member having a mirror surface of one of a curved surface shape and a planar surface shape for detecting assembly performance in the case, the mirror surface being disposed on a side opposite to an optical surface for imaging the image information, the inspection method comprising detecting one of a shift of posture and a distortion of the reflecting member by projecting a light beam from light source means to the mirror surface of the reflecting member and utilizing reflection light from the mirror surface.

According to the present invention, even if the imaging optical element including multiple reflection type optical elements is housed and held in the case, it is easy to measure and inspect the change in shape of each optical element and the assembly error.

Further features of the present invention become apparent from the following description of exemplary embodiments with reference to the attached drawings.

DESCRIPTION OF THE EMBODIMENTS

Figure 1:
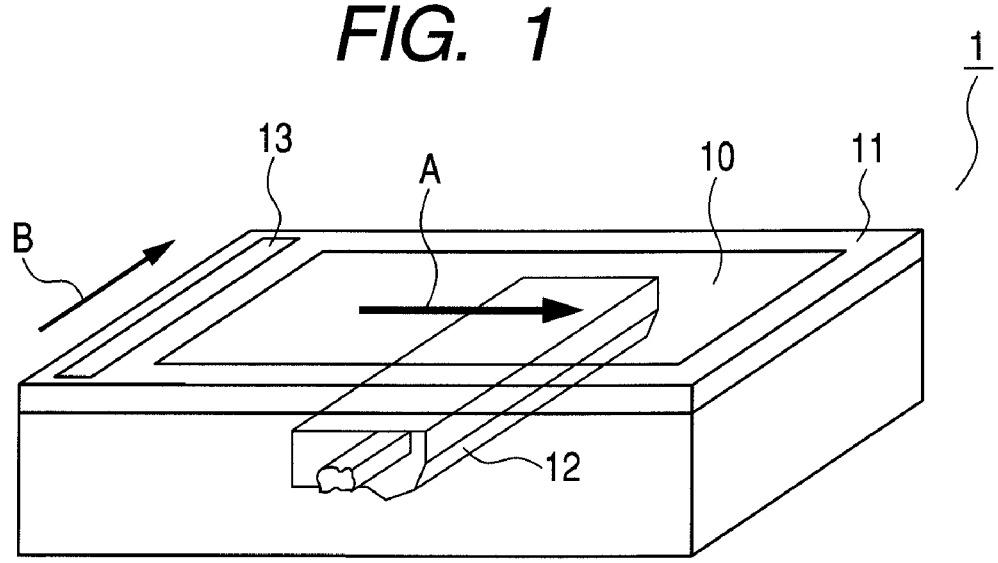
FIG. 1 is an outline view of an image reading apparatus according to Embodiment 1 of the present invention.

Preferred embodiments of the present invention will now be described in detail in accordance with the accompanying drawings.

An imaging optical unit of the present invention includes a case and an imaging optical system having multiple reflection type off-axial optical elements, and the imaging optical system is housed in the case. Each of the multiple off-axial optical elements has a mirror surface of a curved surface shape or a planar surface shape on a side opposite to an optical surface for an imaging action, and the mirror surface is used for detecting assembly performance.

Hereinafter, with reference to the attached drawings, embodiments of the present invention are described.

Embodiment 1

Hereinafter, the embodiments of the present invention are described. First, a manner of attaching an off-axial optical element having an off-axial reflection surface to the imaging optical system (off-axial optical system) is illustrated.

Note that the same members or members having the same function are denoted by the same reference numeral so as to avoid confusion.

FIG. 1 is an outline view of an image reading apparatus according to Embodiment 1 of the present invention.

In FIG. 1, numeral 1 denotes the image reading apparatus. An original 10 has an image formed thereon and is placed on a glass original table 11. In a carriage (unit) 12, an imaging optical system (not shown) for reading the original 10, multiple reflection mirrors (not shown), an illumination system (not shown) for illuminating the original 10, and the like are housed. Numeral 13 is a white plate.

In the image reading apparatus 1 illustrated in FIG. 1, the carriage 12 is first positioned below the white plate 13 and reads the white plate 13 for performing shading so as to determine references of brightness and density. Next, the carriage 12 scans image information of the original 10 placed on the original table 11 in a direction of an arrow A so as to read the image information in a line sequential manner.

Note that a direction perpendicular to the direction of the arrow A on a surface of the original 10 is a main scanning direction (direction of an arrow B), and the direction of the arrow A is a sub scanning direction.

A sub scanning cross section is a plane having a normal in the main scanning direction. A main scanning cross section is a plane that is perpendicular to the sub scanning cross section and is parallel to the sub scanning direction.

Figure 2:
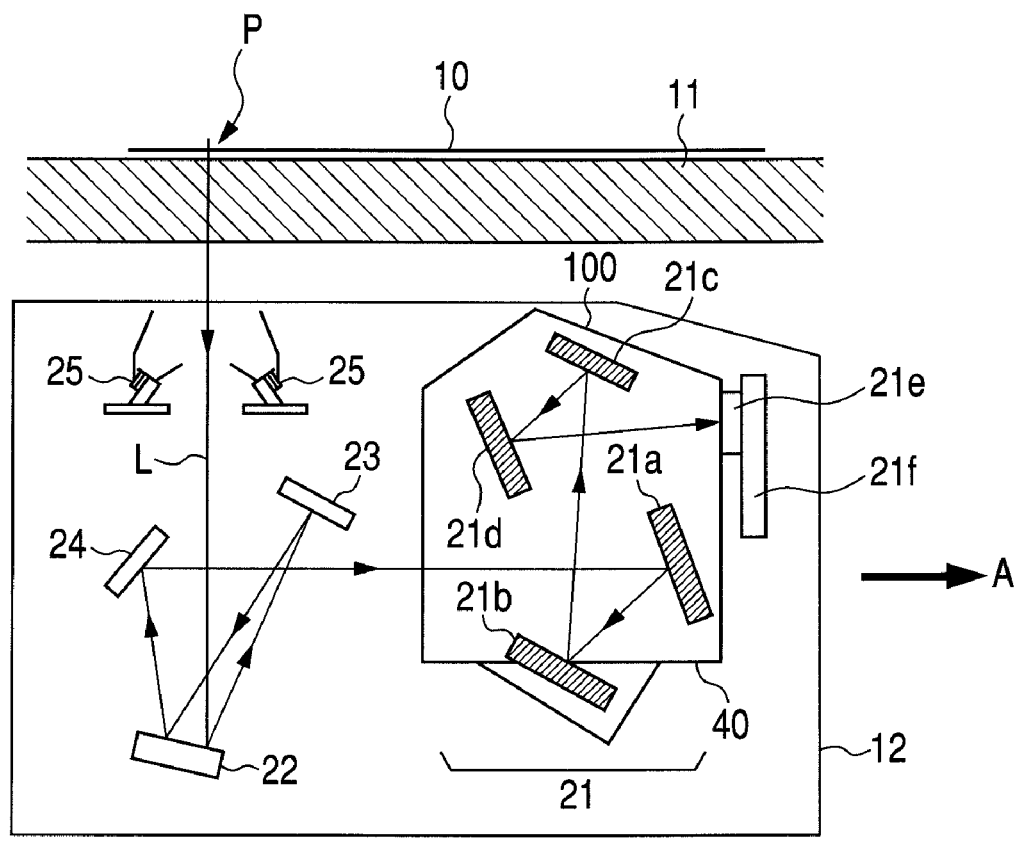
FIG. 2 is a diagram illustrating a carriage of the image reading apparatus according to Embodiment 1 of the present invention.

FIG. 2 is a schematic diagram of a main part illustrating an inside of the carriage 12 illustrated in FIG. 1.

As illustrated in FIG. 2, an illumination system 25 for illuminating the original 10, multiple reflection mirrors 22, 23 and 24 for reflecting a light beam from the original 10, and an imaging optical device 100 for reading the image information of the original 10 are arranged inside the carriage 12. The imaging optical device 100 includes a case 40 and an imaging optical system 21 housed and arranged inside the case.

The imaging optical system 21 includes four reflecting members each of which has an off-axial reflection surface and is made of an optical resin material, that is, reflection type off-axial optical elements (off-axial reflecting mirrors) 21a, 21b, 21c and 21d.

The off-axial optical elements 21a, 21b, 21c and 21d do not have a common optical axis. Such a non-coaxial optical system is called an off-axial optical system, here. The off-axial optical system is defined as an optical system including a curved surface in which a surface normal at an intersection of a constitution surface and a reference axis does not exist on the reference axis (i.e., off-axial curved surface) when the reference axis is considered to be along the light beam passing through a center of image and a center of pupil. In this case, the reference axis has a bent shape.

The reflection type off-axial optical elements 21a, 21b, 21c and 21d are housed in the case and are fixed and held to the case 40 by adhesive. Note that the number of reflecting members in the present invention is not limited to four. There may be provided one or multiple reflecting members.

In addition, pixels are arranged in line in the main scanning direction at the imaging position of the imaging optical system 21, which are arranged in four rows in the sub scanning direction as a photoelectric conversion element that is a line sensor 21e disposed on an electric substrate 21f.

The line sensor 21e has the arrangement of four rows (lines) including red (R), green (G) and blue (B) lines of three primary colors plus a special line of black (BK). However, the number of lines is not limited thereto in this embodiment. It is also possible to use a monochrome line sensor.

The carriage 12 scans in the direction of the arrow A of FIG. 2, that is, in the sub scanning direction. In the scanning, when the carriage 12 is positioned just below a reading position P of the original 10 placed on the original table 11, the light beam containing image information of the surface of the original illuminated by the illumination system 25 is reflected by the three reflection mirrors 22, 23 and 24, and is led to the imaging optical system 21.

Here, the illumination system 25 includes a light source having a reflecting mirror and an LED element, and therefore has a merit that heat generation and power consumption are controlled to be lower than those of a conventional xenon tube or the like. The LED element is a white color LED, which emits white color light by a single element. It is difficult to obtain sufficient light amount by only a single white color LED as much as the conventional xenon tube, and hence multiple white LEDs are arranged in the main scanning direction so as to obtain necessary light amount. In this embodiment, the white LEDs are arranged in two rows so as to sandwich a reading optical axis L of the imaging optical system 21.

Each of the three reflection mirrors 22, 23 and 24 is a planar surface mirror made of glass fixed in the carriage 12. Among the three reflection mirrors 22, 23 and 24, the reflection mirror 22 is adapted to reflect the light beam directly from the surface of the original and also to reflect the light beam reflected by the reflection mirror 23 so as to direct the light beam toward the reflection mirror 24. Thus, the structure can be more compact than the structure using four reflection mirrors.

The light beam that has entered the imaging optical system 21 is reflected by the above-mentioned off-axial optical elements 21a, 21b, 21c and 21d each having the reflection type off-axial surface, and forms an image on the line sensor 21e. The light beam detected by a certain line is also detected by other lines before and after the reading position P when the scanning is performed. Further, the read signals are synchronized by a synchronizing portion (not shown), whereby information pieces of different colors of the same position P read at slightly different timings are synchronized for reproducing the image information correctly.

As described above, the imaging optical system 21 in this embodiment uses the off-axial optical system.

In general, in a case where the off-axial reflection surface is a reflection surface made up of a free-form curved surface, the manufacturing process thereof is complicated if the reflection surface is manufactured using an ordinary glass material.

Therefore, there is known a manufacturing method therefor by molding of an optical resin material such as polycarbonate, acrylic, polyolefin, or the like. This method has a merit that the surface shape can be designed easily, and that the manufacturing process can be facilitated after the mold is made once.

The optical resin material can be formed easily to determine the shape of the optical element by using an injection molding method or the like, but stiffness thereof is not as high as the conventional lens or mirror made of glass or a metal.

Therefore, the reflection type off-axial optical system is required to have high accuracy with respect to a deformation or a positional error of the optical element.

A change in optical performance (sensitivity) with respect to an error in the reflection type off-axial optical system is about twice the case of using a transmission optical element.

In the case of the transmission optical element, it is possible to devise the both sides of the optical element so as to control a changing power (refraction power). In the case of the reflection type optical element, however, the shape itself is the power, and hence the deformation of the surface directly causes a change in power.

Therefore, it is usually possible to adopt the structure of fixing the optical element made of a glass material to the case with a fitting. However, if the structure is adopted for the reflection type off-axial optical system including the optical element made of optical resin, the optical element may be deformed. Therefore, it is necessary to hold the optical element significantly softly.

However, if the optical element is held significantly softly, the optical element may sway due to a vibration when the original is scanned in the main scanning direction and in the sub scanning direction, with the result that a good image may not be obtained. In the worst condition, the optical element may be removed from the case.

In general, it is possible to adopt a method involving fixing a holder member for holding the optical element to the case with the fitting or by using adhesive.

The method involving fixing with the fitting can provide the same holding pressure every time. The fixing method by using adhesive can also provide a stable fixed state if amount of the adhesive and a bonding position are controlled to be the same every time.

An ultraviolet curing adhesive can be cured to have practical strength when irradiated with ultraviolet rays for a predetermined period of time. The optical resin is deformed a little by a tensile force when cured for bonding, but the deformation amount can be controlled to be much smaller than that in the case of fixing with the fitting. A stable fixing performance can be obtained by applying a predetermined amount of adhesive to a predetermined positioning part of the optical resin, positioning the optical resin to the case, and irradiating a predetermined intensity of ultraviolet rays for a predetermined period of time.

Therefore, adhesive is used for holding the optical element in the case in this embodiment.

When the holder member holding the optical element is assembled in the case, and finally optical performance of the imaging optical device as the imaging optical unit is checked, good optical performance may not be obtained for a certain reason.

It is considered that there are multiple factors including a processing error, an assembly error, and the like. In contrast, the case and the optical element are both manufactured by an injection molding process using molds, and hence have little variation. Other factors may include a positioning error when the optical element is fixed, and an error of the amount of the adhesive or the period of time for irradiation.

However, it is difficult to distinguish whether the cause is the positioning error of the optical element due to the assembly error or an adhesive malfunction from the performance of the imaging optical unit (imaging optical device) after the imaging optical unit is assembled. It is also difficult to specify the optical element that causes the malfunction.

Therefore, in this embodiment, the imaging optical unit (imaging optical device) has the structure as described below, whereby positional error of each optical element in the case and a deformation of the optical surface can be inspected easily in the state where the optical elements are housed in the case.

First, in this embodiment, an appearance of the four reflection type off-axial optical elements 21a, 21b, 21c and 21d of the imaging optical system 21 and a manner of assembling the four reflection type off-axial optical elements to be a unit as the imaging optical system 21 are described with reference to FIGS. 3 and 4.

Figure 3:
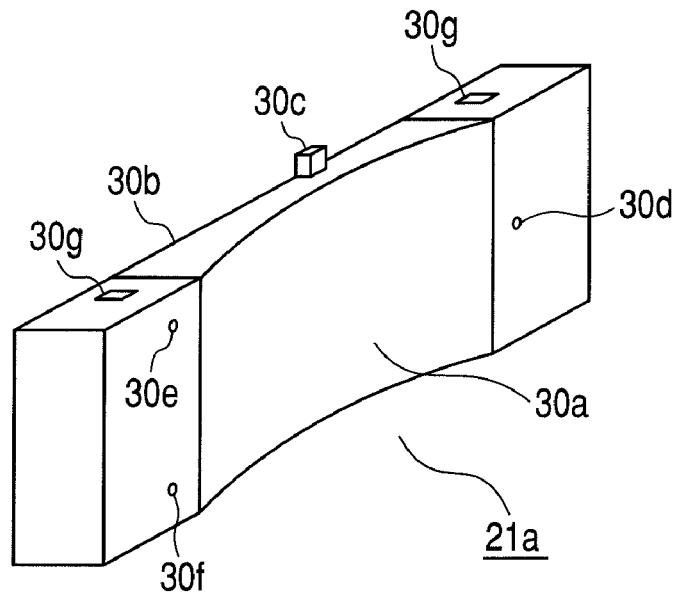
FIG. 3 is a diagram illustrating an appearance of an off-axial optical element.

FIG. 3 is an outline view illustrating an appearance of one reflection type off-axial optical element. Note that one reflection type off-axial optical element 21a is selected as a representative from the multiple reflection type off-axial optical elements 21a, 21b, 21c and 21d and is described in this embodiment.

The reflection type off-axial optical element 21a has an optical surface (optical performance surface) 30a that is processed by vapor deposition of aluminum on a surface thereof and is optimized so as to reflect light efficiently and to perform an imaging action.

In addition, the reflection type off-axial optical element 21a has a mirror surface (mirror surface part) 30b having a curved surface shape or a planar surface shape for detecting the assembly performance formed on a side opposite to the optical surface 30a (hereinafter also referred to as a "back side").

In this embodiment, the mirror surface 30b has a planar surface shape.

The mirror surface described here means abrasively finished surface or the equivalent thereto. When an average value of a surface roughness degree of the mirror surface is denoted by Ra, the following conditional expression is satisfied.

$$Ra \leq 0.02 \, \mu m \quad (1)$$

If the conditional expression (1) is satisfied, it is easy to measure the mirror surface utilizing Newton's rings in the measurement using the interferometer as an inspection unit described later, for example. If the conditional expression (1) is not satisfied, the mirror surface may not be measured correctly.

As a matter of course, if the mirror surface is polished with higher accuracy, more accurate measurement can be performed. If the following conditional expression (1a) is satisfied, it is possible to be used in the surface having a normal optical performance.

$$Ra \leq 0.01 \, \mu m \quad (1a)$$

The reflection type off-axial optical element 21a is provided with multiple positional references for positioning the same to the case with a correct posture. In FIG. 3, a main scanning direction positioning pin 30c is provided for positioning the position in the case in the main scanning direction (longitudinal direction). This pin 30c abuts the main scanning direction positioning portion in the case so as to set a correct position.

In addition, as illustrated in FIG. 3, sub scanning direction positioning portions 30g are disposed at two parts in the longitudinal direction for positioning in the sub scanning direction and preventing rotation of the surface. Further, optical axis direction positioning pins 30d, 30e and 30f are disposed on the surfaces that are the same as the optical surface 30a, and are set in strict accuracy so as to maintain spaces between the off-axial optical elements of the imaging optical system and to maintain the same height.

Figure 4:
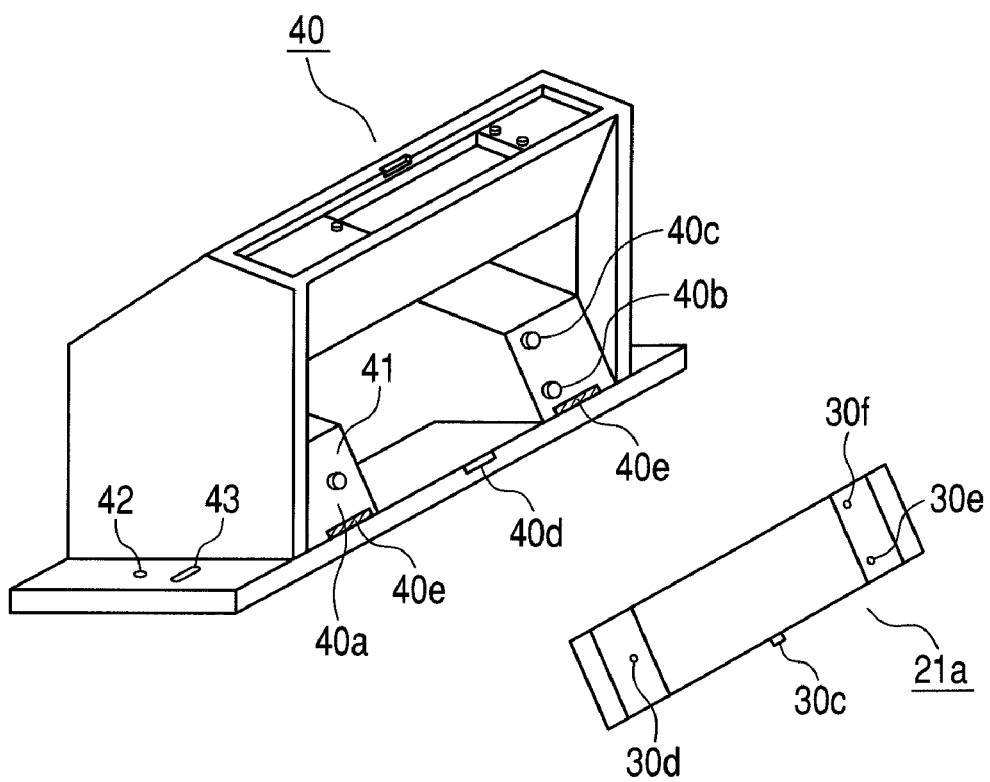
FIG. 4 is a diagram for describing attachment of the off-axial optical element with a case.

FIG. 4 is an explanatory diagram illustrating the case 40 and a manner of attaching the reflection type off-axial optical element 21a to the case 40.

Note that the manner of attaching other reflection type off-axial optical elements 21b, 21c and 21d to the case 40 is substantially the same as the case of the reflection type off-axial optical element 21a.

In FIG. 4, the case 40 is devised for the positioning so that the four off-axial optical elements 21a, 21b, 21c and 21d can be positioned accurately. As illustrated in FIG. 4, biasing surfaces 41 are prepared at three positions 40a, 40b and 40c corresponding to the optical axis direction positioning pins 30d, 30e and 30f of the reflection type off-axial optical element 21a, and each pin of the off-axial optical element 21a abuts the corresponding surface.

In this case, the main scanning positioning pin 30c engages with a main scanning direction positioning hole 40d while the sub scanning direction positioning portions 30g engage with positioning portions 40e for positioning in the main scanning direction and in the sub scanning direction. When the reflection type off-axial optical element 21a is attached to the case 40, predetermined amount of adhesive is applied to the three positions 40a, 40b and 40c in advance.

The adhesive used here is an ultraviolet curing type, which is irradiated with ultraviolet rays for a predetermined period of time after the reflection type off-axial optical element 21a is set in the case 40 or simultaneously. It is desirable to perform the irradiation simultaneously as much as possible, so as to prevent an inclination due to a tensile force during the curing process.

Other three surfaces are also bonded in the same manner. After the four reflection type off-axial optical elements 21a, 21b, 21c and 21d are bonded, the imaging optical system 21 is fixed with a screw at a screw fixing hole 42 after positioning a guide hole 43 to a positioning pin of the carriage part (not shown).

Next, an inspection method for the imaging optical system according to the present invention is described.

It is supposed that the case has occurred where acceptable imaging performance cannot be obtained after the four reflection type off-axial optical elements 21a, 21b, 21c and 21d are bonded to a part of the case 40 as described above. In this case, it is difficult to measure distortions of the optical surfaces of the four reflection type off-axial optical elements 21a, 21b, 21c and 21d because the optical surfaces face inward.

In addition, if a positional shift occurs with respect to the reference surface for attachment in the bonding process, it is also difficult to find the surface causing the positional shift from the four surfaces. In addition, if a deformation occurs due to incorrect adhesion, the inner side of the surface cannot be measured externally while the inner side cannot be checked if detached because the state thereof is changed.

In this embodiment, the above-mentioned mirror surface (mirror surface part) 30b provided to each of the back sides of the reflection type off-axial optical elements 21a, 21b, 21c and 21d is utilized. The mirror surface having a planar surface shape is provided to each of the back sides of the off-axial optical elements 21a, 21b, 21c and 21d, and the mirror surface is opened to the outside of the case of the imaging optical system 21.

The reflection type off-axial optical element is an optical element made of optical resin as described above, and can be considered that the top side and the back side are deformed substantially in the same manner if the thickness does not vary extremely.

Therefore, in this embodiment, the state of the mirror surface 30b or the optical surface 30a is inspected by measuring a distortion, a deformation and a shape of the mirror surface 30b of the imaging optical system 21 externally using the inspection unit that is described later.

Figure 5:
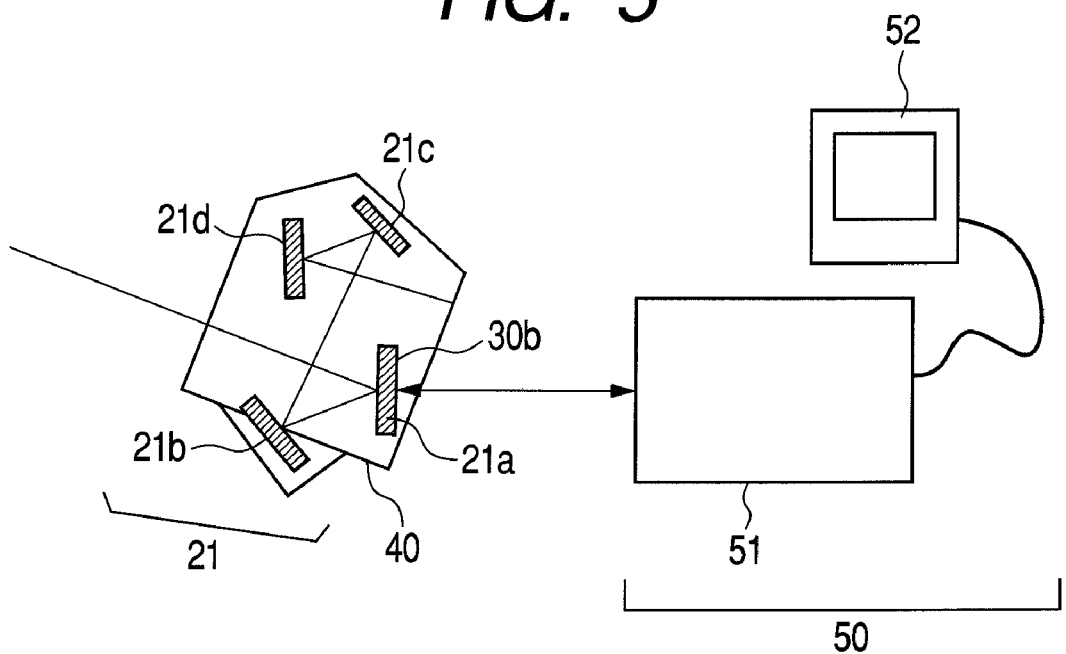
FIG. 5 is a diagram illustrating a manner of measuring an imaging optical system with an interference pattern in Embodiment 1 of the present invention.

FIG. 5 is an explanatory diagram illustrating a manner (inspection method) of measuring the mirror surface of one off-axial optical element of the imaging optical system using the inspection unit.

In FIG. 5, an inspection unit 50 includes an interferometer 51 and a monitor 52, for inspecting a state of the mirror surface 30b.

In this embodiment, the interferometer 51 is prepared so as to face correctly to the mirror surface 30b on the back side of the reflection type off-axial optical element 21a as illustrated in FIG. 5. An interference pattern is generated by returning light (reflection light) from the mirror surface 30b on the back side of the reflection type off-axial optical element 21a, and a manner thereof is displayed on the monitor 52.

Further, the interference pattern is compared with an "original interference pattern" in the case of correct adhesion that is measured in advance. If a pattern equal to the "original interference pattern" is observed, the adhesion of the surface has been performed correctly. In the case of a pattern substantially different from the same, the adhesion has not been performed correctly. If there is observed a state where the surface is pulled in one direction, the amount of the adhesive may be different among the three points (three points 40a, 40b, 40c illustrated in FIG. 4) or the bonded position may be shifted. Otherwise, even if the interference pattern is the same as the "original interference pattern", if it is necessary to incline the case 40 from the original posture when the interference pattern is generated, the off-axial optical element 21a may be attached in an inclined manner.

In this way, the surface on which a bonding or attaching error occurs can be checked without detaching the reflection type off-axial optical element 21a from the case 40. Only the necessary part is rebonded, whereby the correction can be performed in minimum time using minimum components.

The reflection type off-axial optical element 21a is exemplified for describing the inspection method in this embodiment, but the inspection method can be performed similarly for the other reflection type off-axial optical elements 21b, 21c and 21d.

In addition, the back side of the reflection type off-axial optical element 21a is used as the mirror surface in this embodiment, but can be a surface on which aluminum or other metal is formed by vapor deposition or a surface to which the same is applied (surface made of an evaporated film or a coated film having a reflection action). Thus, reflection factor is increased so that a merit for measurement is obtained. In addition, if the vapor deposition is performed on both the top side and the back side, the deformation due to the vapor deposition can be relieved. Thus, in this embodiment, the inspection unit using the inspection method described above is incorporated in the image reading apparatus, and postures of the four off-axial optical elements are adjusted based on a result of the detection from the inspection unit so that the image reading apparatus with high performance and a simple structure can be obtained.

Embodiment 2

Figure 6:
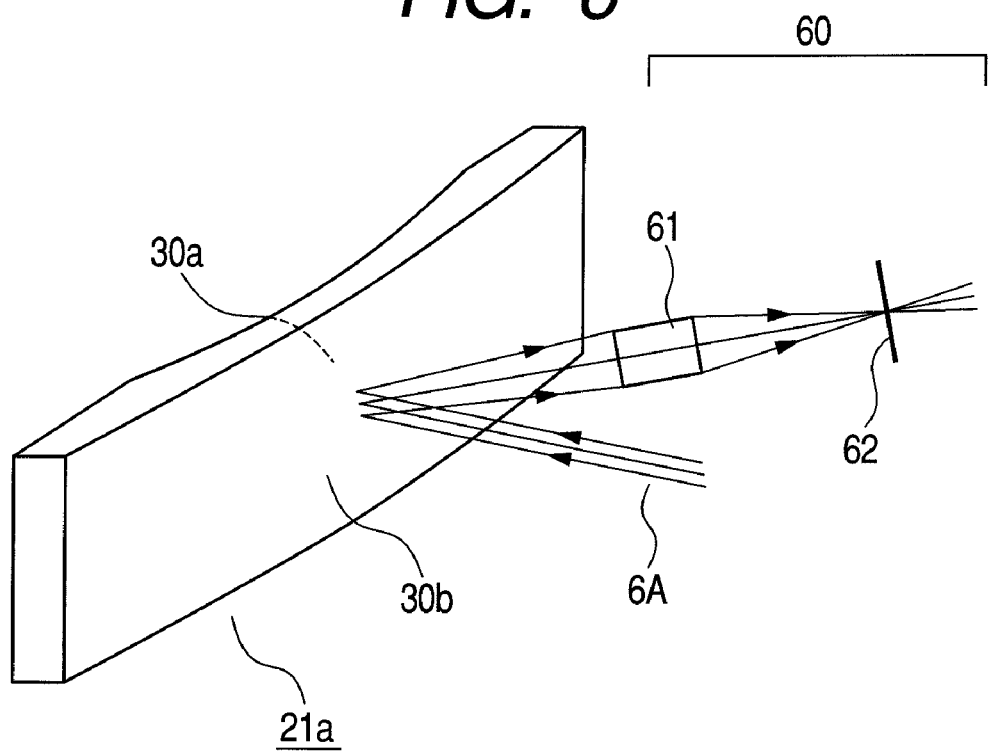
FIG. 6 is a diagram illustrating a manner of measuring a state of a mirror surface on a back side in Embodiment 2 of the present invention.

FIG. 6 is an explanatory diagram illustrating a manner (inspection method) of measuring a reflection type off-axial optical element according to Embodiment 2 of the present invention.

This embodiment is different from Embodiment 1 described above in that the mirror surface 30b on the back side of the reflection type off-axial optical element 21a is formed to have a spherical surface shape performing a condensing action or a diverging action. Other structure and optical action are the same as those of Embodiment 1 so that the same effect can be obtained.

More specifically, in FIG. 6, the reflection type off-axial optical element 21a has the mirror surface (mirror surface part) 30b on the back side made of the spherical surface shape performing the condensing action or the diverging action.

Further, the mirror surface 30b having the curved surface shape is formed to have the same shape as an absolute value of an on-axis power of the optical surface 30a.

In this embodiment, the back side of the off-axial optical element 21a having the off-axial surface is set with accuracy higher than or equal to that of the mirror surface having the spherical surface, as illustrated in FIG. 6.

For instance, a light beam 6A, which is emitted from a light source unit (not shown) and is collimated to be a parallel light beam, is made to enter the mirror surface 30b having the spherical surface shape. The mirror surface 30b has the spherical surface shape and is a convex surface in this case, and hence the light beam expands in a little diffusing manner. The light beam is condensed on a detection surface (light beam detection surface) 62 by an imaging lens (condenser lens) 61.

The detection surface 62 is constituted by utilizing an optical element such as a photodiode (PD) producing an output signal that varies according to light amount or an optical element such as a position sensitive detector (PSD) for obtaining positional information according to the condensing position on the detection surface 62. Then, an electric signal (detection output value) is obtained from the detection surface 62, whereby a condensed state of the reflection light from the back side is obtained from a variation of the output or the positional information of the detection surface.

Note that the light source (not shown), the imaging lens 61, and the element of the PD or the PSD for the detection surface 62 constitute an element of the inspection unit 60.

In this embodiment, a detection output value A is measured in advance in a standard condition under which the off-axial optical elements 21a to 21d are attached to the case 40. Further, if a detection output value B in a case of a certain malfunction is compared with the detection output value A, the detection output value B must have decreased from the detection output value A in the standard condition.

Figure 7A:
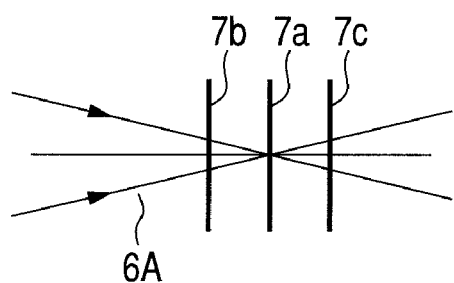
FIG. 7A is a diagram for describing an inspection method for knowing a changed state in a curvature of a surface from a result of detection.

For instance, as illustrated in FIG. 7A, a peak of the detection output value appears at a position 7b or 7c before or after a standard position 7a of the detection surface. In other words, if the condensed position exists at the position 7b or 7c, a variation of curvature of the mirror surface 30b having the spherical surface shape on the back side of the off-axial optical element 21a can be known from the shift amount and a predetermined focal length of the imaging lens 61. Thus, it is possible to discriminate whether or not the measured mirror surface 30b is deformed.

Figure 7B:
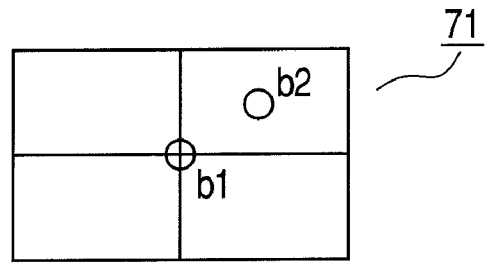
FIG. 7B is a diagram for describing an inspection method for knowing an off-center and a positional shift of the surface from a result of detection.

In addition, as illustrated in FIG. 7B, if a sensor such as a PSD 71 is used for the detection surface 62, an inclination and the like of the off-axial optical element 21a can be detected by detecting a displacement state b2 that is a state shifted from the imaging position in a standard condition b1.

The back side of the off-axial optical element is set to have a convex spherical surface shape, but may be set to have a concave surface. However, it should be noted that if the back side of the off-axial optical element is set to have a concave surface, a problem such as a deformation or the like of the surface may occur in the molding process when a difference of thickness becomes large between a center part and a peripheral part in the main scanning direction.

In addition, on the prediction of a combination with the imaging lens 61 described above, for example, it is of course possible to set an aspherical surface or a surface having the same shape but opposite to the optical surface concerning convex and concave, if necessary. Combining the imaging lens 61 with the shape as described above, the condensing action onto the detection surface is improved.

Thus, in this embodiment, light is projected to the mirror surface 30b having the spherical surface shape, and the reflection light from the mirror surface 30b is utilized for detecting the assembly accuracy of the multiple reflection type off-axial optical elements 21a to 21d in the case 40 by the above-mentioned inspection unit. Consequently, the same effect as Embodiment 1 can be obtained.

Embodiment 3

Figure 8:
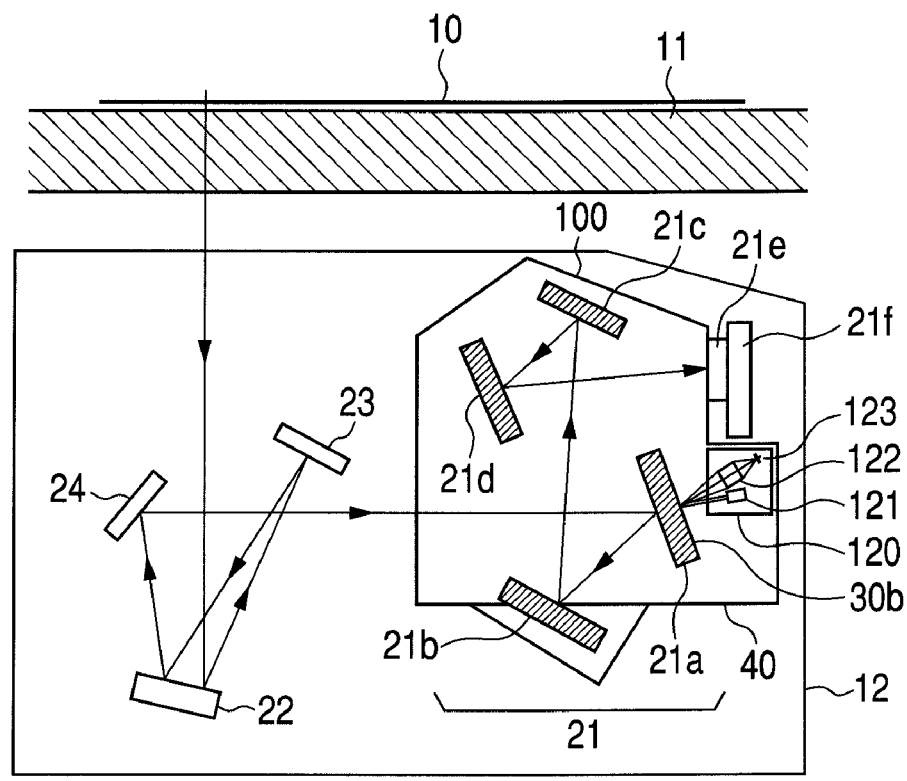
FIG. 8 is a diagram illustrating an image reading apparatus incorporating an inspection method for knowing a state of a surface according to Embodiment 3 of the present invention.
Figure 9:
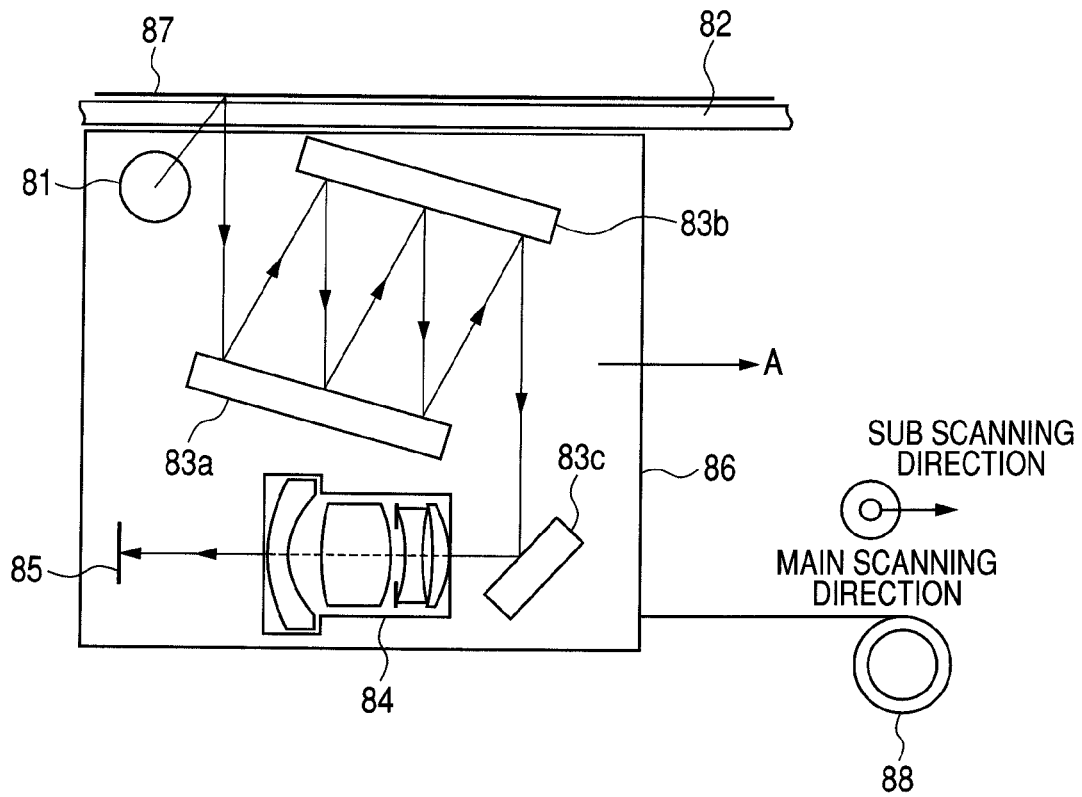
FIG. 9 is a schematic diagram of a main part of a conventional image reading apparatus of an integrated carriage type.
Figure 10:
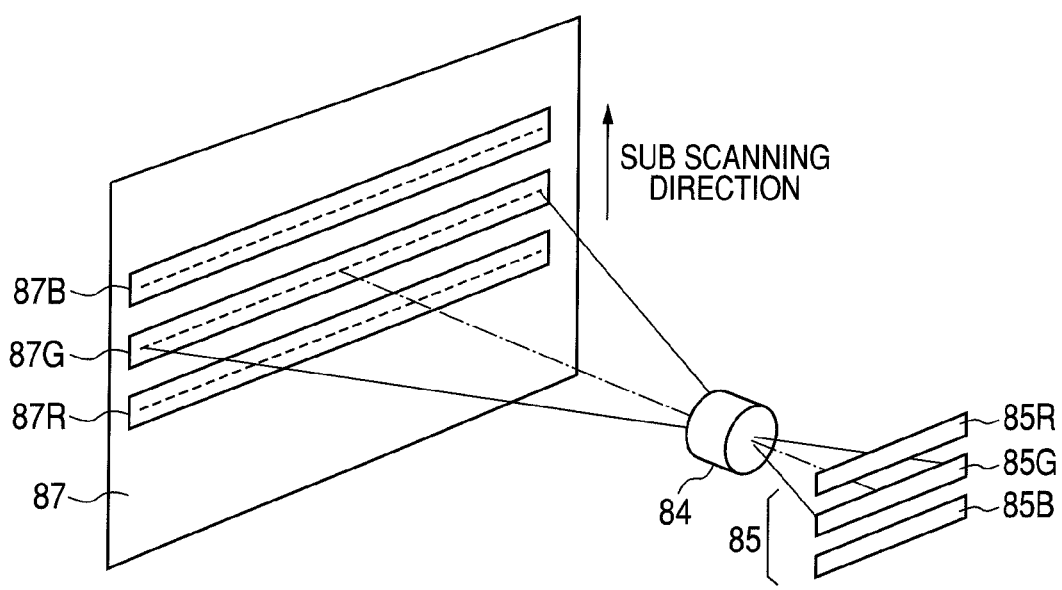
FIG. 10 is a diagram illustrating a fundamental structure of an imaging optical system of the conventional image reading apparatus.

FIG. 8 is a schematic diagram of a main part of an image reading apparatus of Embodiment 3 of the present invention.

The image reading apparatus according to this embodiment has a structure in which the imaging optical device 100 and the inspection method described above are incorporated, and a distortion of the off-axial optical element 21a during continuous operation can be monitored by a distortion monitoring portion 120.

More specifically, in FIG. 8, the carriage 12 has the case 40 in which the imaging optical system 21 made up of the four reflection type off-axial optical elements 21a to 21d, the line sensor 21e, the substrate 21f and the like are housed.

The back side of the reflection type off-axial optical element 21a constituting an element of the imaging optical system 21 is finished to have the mirror surface of the spherical surface shape (mirror surface state) 30b. In addition, the distortion monitoring portion 120 for monitoring the distortion of the reflection type off-axial optical element 21a is disposed inside the case 40, whereby a shape of the reflection type off-axial optical element 21a is monitored on a monitor (not shown).

Note that it is possible to adopt a structure in which the distortion monitoring portion 120 monitors a shape of at least one reflection type off-axial optical element among other reflection type off-axial optical elements 21b, 21c and 21d without limiting to the reflection type off-axial optical element 21a.

The distortion monitoring portion 120 includes a light source part 121 having a semiconductor laser for emitting a parallel light beam and a collimator lens, an imaging lens 122 for receiving the reflection light from the mirror surface 30b on the back side of the reflection type off-axial optical element 21a, and a displacement detector 123. Thus, as described above in Embodiment 2, a distortion of the off-axial optical element 21a can be monitored on a monitor (not shown) based on a variation in an output signal of the displacement detector 123.

For instance, if temperature in the apparatus has increased substantially due to continuous operation for a long time, or if ambient temperature is high, the reflection type off-axial optical element made of optical resin may have a distortion, which causes deterioration of image quality.

Therefore, based on the detected signal, a message urging caution is displayed on a monitor of the apparatus, the apparatus is stopped temporarily for decreasing temperature, or an inside cooling fan is rotated for decreasing inside temperature, whereby stable image reading can be realized.

Further, instead of bonding any one of the reflection type off-axial optical elements directly to the case 40, a holder member holding the same is attached to the case 40 indirectly via an attaching plate. Then, a reflection plate is bonded there, and an electrical correction mechanism is incorporated for automatically controlling a posture of the attaching plate, whereby the image reading apparatus can always provide high image quality.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2008-122209, filed May 8, 2008, which is hereby incorporated by reference herein in its entirety.

What is claimed is:

1. An inspection method for an imaging optical unit used in an image reading apparatus for obtaining image information by imaging the image information on a photoelectric conversion element,
the imaging optical unit including a case and an imaging optical system disposed in the case,
the imaging optical system including a reflecting member having a mirror surface of one of a curved surface shape and a planar surface shape for detecting assembly performance in the case, the mirror surface being disposed on a side opposite to an optical surface for imaging the image information,
the inspection method comprising detecting one of a shift of posture and a distortion of the reflecting member by projecting a light beam from light source means to the mirror surface of the reflecting member and utilizing reflection light from the mirror surface.

2. An inspection method according to claim 1, wherein the detecting is performed by reflecting the light beam from the light source means by the mirror surface, condensing the reflection light by a condenser lens onto a light beam detection surface, and detecting a condensing position on the light beam detection surface.

3. An inspection method according to claim 1, wherein the detecting is performed by projecting the light beam to the mirror surface, utilizing the reflection light from the mirror surface to generate an interference pattern, and measuring the interference pattern.

4. An adjustment method for an imaging optical unit used in an image reading apparatus for obtaining image information by imaging the image information on a photoelectric conversion element, the adjustment method comprising:
detecting a shift of posture of a reflecting member having a mirror surface by the inspection method according to claim 1; and
adjusting a posture of an optical element constituting the imaging optical unit based on a result of the detecting.

5. An imaging optical unit used in an image reading apparatus for obtaining image information by imaging the image information on a photoelectric conversion element, the imaging optical unit comprising:
a case; and
an imaging optical system disposed in the case, wherein:
the imaging optical system includes a reflecting member;
the reflecting member has a mirror surface of one of a curved surface shape and a planar surface shape for detecting assembly performance in the case on a side opposite to an optical surface for imaging the image information;
a light source for projecting a parallel light beam to the mirror surface; and
a detector for receiving the parallel light beam reflected by the mirror surface and detecting one of a shift of posture and a distortion of the reflecting member having the mirror surface so as to output information about one of the shift of posture and the distortion.

6. An imaging optical unit according to claim 5, further comprising:

a control portion for controlling the imaging optical unit based on the information output from the detector.

7. An imaging optical unit according to claim 5, wherein when an average value of a surface roughness degree of the mirror surface formed on the side opposite to the optical surface for imaging the image information of the reflecting member is denoted by Ra, the following conditional expression is satisfied:

$Ra \leq 0.02 \, \mu m.$

8. An imaging optical unit according to claim 5, wherein the mirror surface of the curved surface shape includes a mirror surface performing one of a condensing action and a diverging action.

9. An imaging optical unit according to claim 5, wherein the curved surface shape includes a spherical surface shape.

10. An imaging optical unit according to claim 5, wherein the mirror surface has the same absolute value of an on-axis power as that of the optical surface.

11. An imaging optical unit according to claim 5, wherein the mirror surface has one of an evaporated film and a coated film having a reflecting action formed thereon.

12. An imaging optical unit according to claim 5, wherein the reflecting member is made of optical resin, which is bonded and held in the case.

\* \* \* \* \*